(12) United States Patent
Brown et al.

(10) Patent No.: US 6,361,514 B1
(45) Date of Patent: Mar. 26, 2002

(54) UNIVERSAL ANKLE SPLINT

(75) Inventors: Ivan E. Brown, Spirit Lake, IA (US); Robert D. Petrosenko, Batesville, IN (US); Teryle L. Kounkel; Rebecca A. Mills, both of Spirit Lake, IA (US)

(73) Assignee: Brown Medical Industries, Spirit Lake, IA (US)

( * ) Notice: Subject to any disclaimer, the term of this patent is extended or adjusted under 35 U.S.C. 154(b) by 0 days.

(21) Appl. No.: 09/792,743

(22) Filed: Feb. 23, 2001

(51) Int. Cl.[7] .................................................. A61F 5/00
(52) U.S. Cl. ............................ 602/23; 602/27; 128/882
(58) Field of Search ................................. 128/846, 869, 128/882, DIG. 20; 602/5, 8, 12, 13, 23, 27

(56) References Cited

U.S. PATENT DOCUMENTS

| | | | | |
|---|---|---|---|---|
| 3,955,565 | A | * 5/1976 | Johnson | 602/12 |
| 4,184,273 | A | * 1/1980 | Boyer | 36/131 |
| 4,217,893 | A | * 8/1980 | Payton | 602/12 |
| 4,505,269 | A | 3/1985 | Davies | |
| 5,833,639 | A | * 11/1998 | Nunes | 602/13 |

* cited by examiner

Primary Examiner—Michael A. Brown
(74) Attorney, Agent, or Firm—Zarley, McKee, Thomte, Voorhees & Sease PLC

(57) ABSTRACT

The universal walking splint movably attachable to the lower leg and foot to substantially immobilize the lower leg and foot. It has a posterior shell for holding a sole insert pad, and a movable and removable arch support attachable to the sole insert pad to allow selective arch support at the proper location under either a right foot or a left foot.

5 Claims, 4 Drawing Sheets

UNIVERSAL ANKLE SPLINT

FIELD OF THE INVENTION

This invention relates to orthopaedic appliances, and more specifically it relates to a universal walking splint used to substantially immobilize the ankle joint and/or lower leg.

BACKGROUND OF THE INVENTION

One of the most common orthopaedic injuries is the ankle sprain. The treatment objective is usually to relieve the pain and to immobilize the joint and the ligaments to promote healing of the torn fibers.

Immobilization is accomplished by a variety of methods. One method is to wrap an elastic bandage around the foot and ankle, occasionally incorporating U-shaped felt pads that are placed so that the soft tissue surrounding the malleolus is compressed to minimize swelling. Crutches are used for partial weight bearing for several days or weeks. The elastic bandage does not afford the complete immobilization needed for solid healing of severely torn ligaments and its use is associated with a higher incidence of reinjury. Daily activities are limited by the associated use of crutches.

A second method of immobilization is the application of a plaster cast with the addition of a walking heel or boot. Plaster casts permit firm immobilization, but require a two- or three-day period of walking with crutches, using extreme care not to bear weight on the cast because to do so may cause it to soften, rendering it useless. Since these casts usually stay on for at least two weeks before they are removed and/or replaced, they cause itching and sometimes dermatitis secondary to perspiration and bacterial overgrowth. As tissue swelling about the ankle decreases and muscle atrophy occurs in the calf, the cast becomes loose and uncomfortable. Thus, the extremity may need to be recasted, entailing more physician time and expense and another period of crutch usage.

Such products are also useful for non-displaced fractures, stress fractures, calcaneal fractures, internally fixed fractures, post-surgical immobilization, and chronic plantar fasciitis. In all these instances, immobilization of the lower leg and ankle joint is essential.

Another more recent method of treatment involves the application to the ankle of various preformed apparatus, such as braces and nonplaster casts. While these advantages have resulted in widespread acceptance, none of the appliances except Davies account for the bilaterality of the extremities, that is left and right side. It is suspected that one reason for the lack of acceptance is the failure of the appliance to account for the bilaterality of the extremities, i.e., left and right sides. When one observes the foot and ankle, it is apparent that there are marked differences between the medial and lateral aspects. First of all, the medial side is larger. Secondly, the first metatarsophalangeal joint is located anteriorly to the fifth metatarsophalangeal joint and is more prominent. Thirdly, there is an arch located on the medial aspect of the foot, but none on the lateral aspect. Fourthly, the medial malleolus is located anteriorly and superiorly to the lateral malleolus. The foregoing anatomical facts would seem to preclude a comfortable fit by any snug fitting cast or apparatus that encases the foot and ankle, but does not incorporate at least some features of bilaterality into its design.

An improvement over these conventional prior art ankle splints is the splint currently manufactured by Brown Medical, Inc. and licensed under U.S. Pat. No. 4,505,269, dated Mar. 19, 1985. In this patent, the walking splint has a discreet, posterior member, a discreet anterior member, a discreet lateral member, and a discreet medial member, all bound by wrapping straps extending across the lower leg and around the foot. While this product is satisfactory, it lacked left-right flexibility. Put another way, with the product described in U.S. Pat. No. 4,505,269, a clinic needed to have left and right units. This, of course, increases expense and the size of inventory needed.

In order to overcome need for substantial inventory to allow immediate fitting of right or left feet, many in the field of orthopaedic appliances have gone to universal right/left splints. One problem with this, however, is that for the unit to be universal, it cannot have an arch support, since the arch supports are in different locations for the right and left foot. To illustrate, one can think of walking in shoes without arch supports. Eventually your feet tire, potentially leading to a host of orthopaedic problems in your feet, knees, hips and back. Thus, the device, which itself began its life as an orthopaedic aid, in fact may often cause orthopaedic problems!

It is, therefore, an object of the present invention to provide a splint for immobilizing the ankle joint and capable of being worn comfortably, which is universal, i.e., can be used with either a right or left foot, but at the same time still have an arch support properly located for either a right or left foot.

It is a further object of this invention to provide such a splint as indicated above with an arch support which is adjustable to allow customizing a universal splint for either the right or left foot.

A further object of this invention is to provide such a splint which is lower in cost to produce, since it uses a universal shell, and therefore requires only a single universal injection mold for manufacture.

SUMMARY OF THE INVENTION

A universal walking splint removably attachable to the lower leg and foot to substantially immobilize the ankle joint, with the universal splint having a universal sole insert pad positioned inside of the splint's posterior shell, and an arch support that is both adjustable and attachable to the sole insert pad to provide a selective arch support when properly located under either the right foot arch or the left foot arch. The arch support pad is a compressible foam material, preferably with an adhesive layer which can be exposed by peeling off a protective cover, allowing the adhesive layer of the arch pad to adhere to the sole insert for proper conformity to the wearer's arch.

DETAILED DESCRIPTION OF THE PREFERRED EMBODIMENT OF THE INVENTION

Shown in FIGS. 1 through 4 are a preferred form of the device 10 of the present invention.

Figure 1:
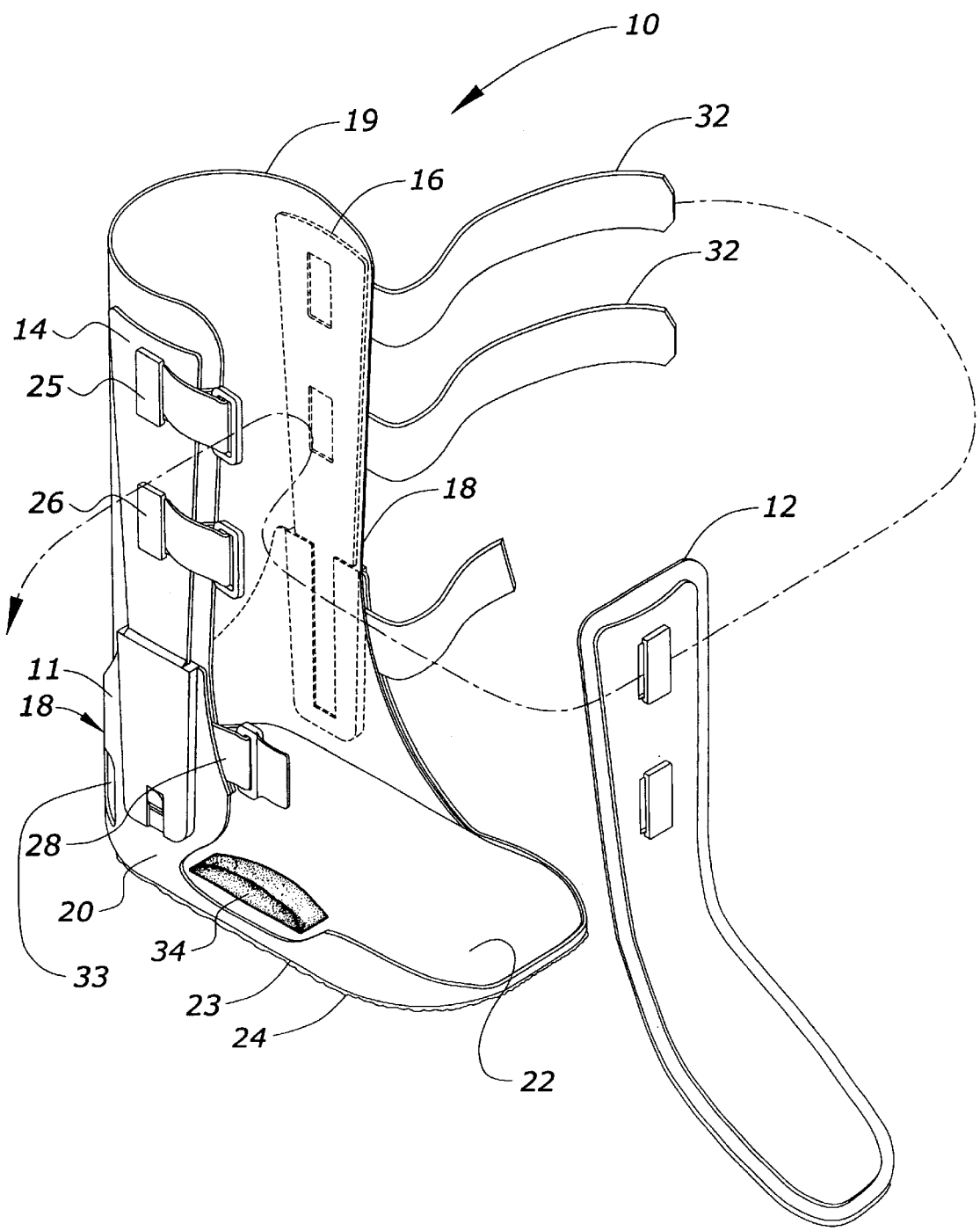
FIG. 1 is an exploded perspective view of the universal splint, ready for application to a left foot.
Figure 2:
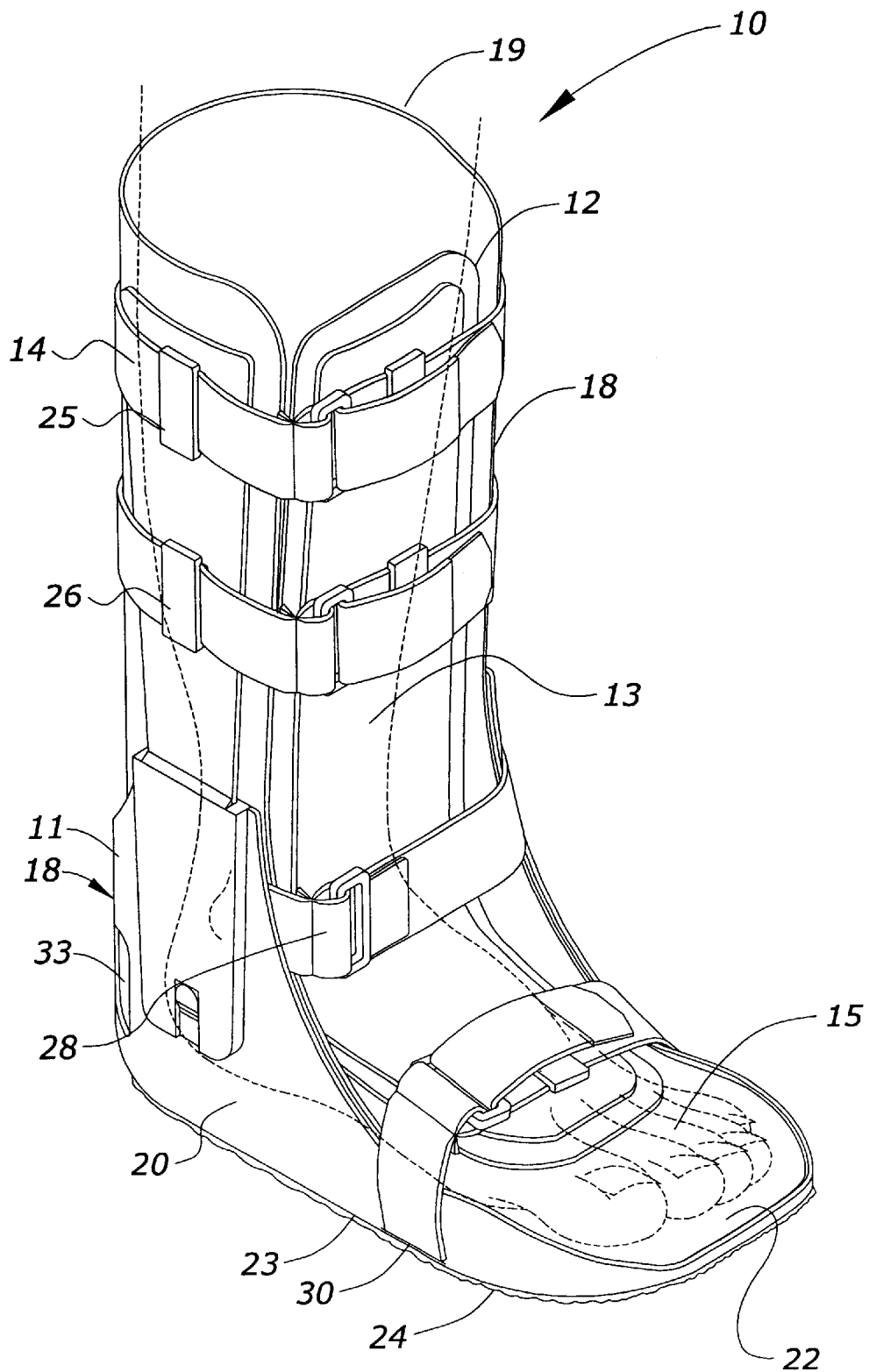
FIG. 2 is a perspective view of the splint of FIG. 1 in place on the lower left leg and foot.

FIG. 1 illustrates a preferred embodiment of an ankle splint 10 made in accordance with the principles of the present invention. The splint comprises a posterior member 11, an anterior member 12, a medial brace 14, and a lateral brace 16. The members and lateral and medial braces are formed so that they encompass and hold firm the lower leg and foot of the patient to substantially immobilize the ankle joint during healing of an ankle sprain or non-displaced fracture. The splint, in its assembled state, positioned on a lower leg 13 and foot 15 of a person is shown in FIG. 2.

The posterior member 11 is the largest component of the splint. The posterior member is generally an L-shaped shell, and includes a vertical portion 18 that partially supports the posterior aspect of the leg from above the heel downwardly to the heel, extending upwardly on the inside and outside of the shell, and integrally formed therewith are lateral and medial supports 14 and 16. The posterior member wraps around the heel to provide an underlying platform portion 20 upon which the foot of the patient rests. The vertical portion 18 is typically comprised of an outer plastic shell. The vertical portion 18 and the platform portion 20 of the posterior member 11 form substantially a right angle. The posterior member 11 has a heel recess formed therein to accommodate the heel of the wearer. Typically, the plastic foot platform portion 20 for an adult is approximately 2.5 centimeters thick. In operation, the calf and lateral and medial sides of the lower leg are further supported by an insert pad 19 which may be made from compressible foam material.

The undersurface 23 of the foot platform portion 20 of the posterior member 11 preferably has a gripping sole 24 formed therein to increase the traction of the surface and minimize the possibility of slipping while walking. This sole 24 forms a separate walking surface of rubber or some other anti-skid material that can be easily affixed to the underside of the posterior member 11. The posterior member 11 has integrally formed in it four slots 25, 26, 28 and 30 for the purpose of retaining four straps 32 that encircle the members to hold them in their correct positions about the lower extremity. The slots 25 and 26 are formed in the lateral 16 and medial 14 supports of the posterior member 11 while the slots 28 and 30 are respectively formed just above the heel and in the foot platform portion 20 approximately under the center of the foot. Straps 32 pass through the slots 25, 26, 28 and 30. Additionally and optionally air circulation slots 33 can be formed in the shell at the base of the heel.

The posterior shell 11, has a strap 32, extending from the medial side of the sole portion 24 to the anterior side of the sole portion 24.

The anterior member 12 has a similar compressible foam attached to it so that the foam conforms more comfortably to the immobilized lower extremity of the front of the leg and the top of the foot.

As depicted in FIGS. 1 and 2, a foam pad sole insert 22 is removably insertable inside of the foot portion of the posterior shell member 11. It, too, like the shell, is of universal configuration so that it can fit fully within the portion of the shell which defines a foot cavity. It is made of a stronger compressible material which can withstand the weight of the patient wearing the universal walking splint 10 and provide cushioning.

Figure 3:
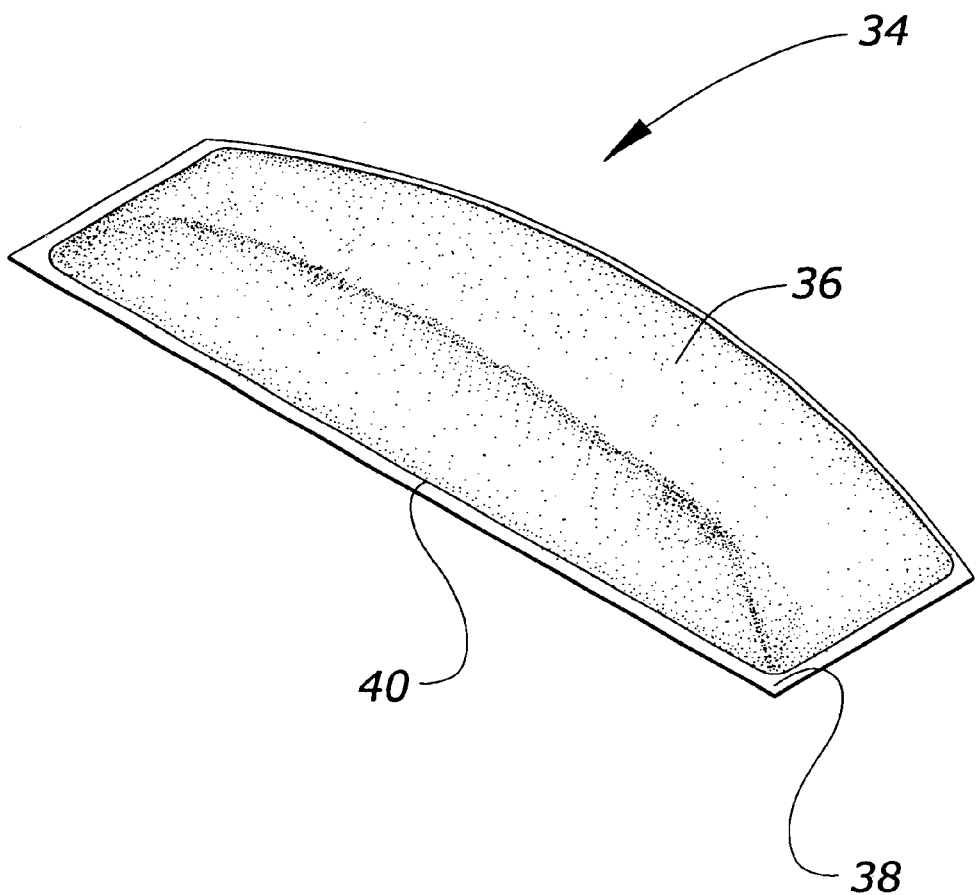
FIG. 3 is a perspective view of the arch support with its peel off protective cover attached.
Figure 4:
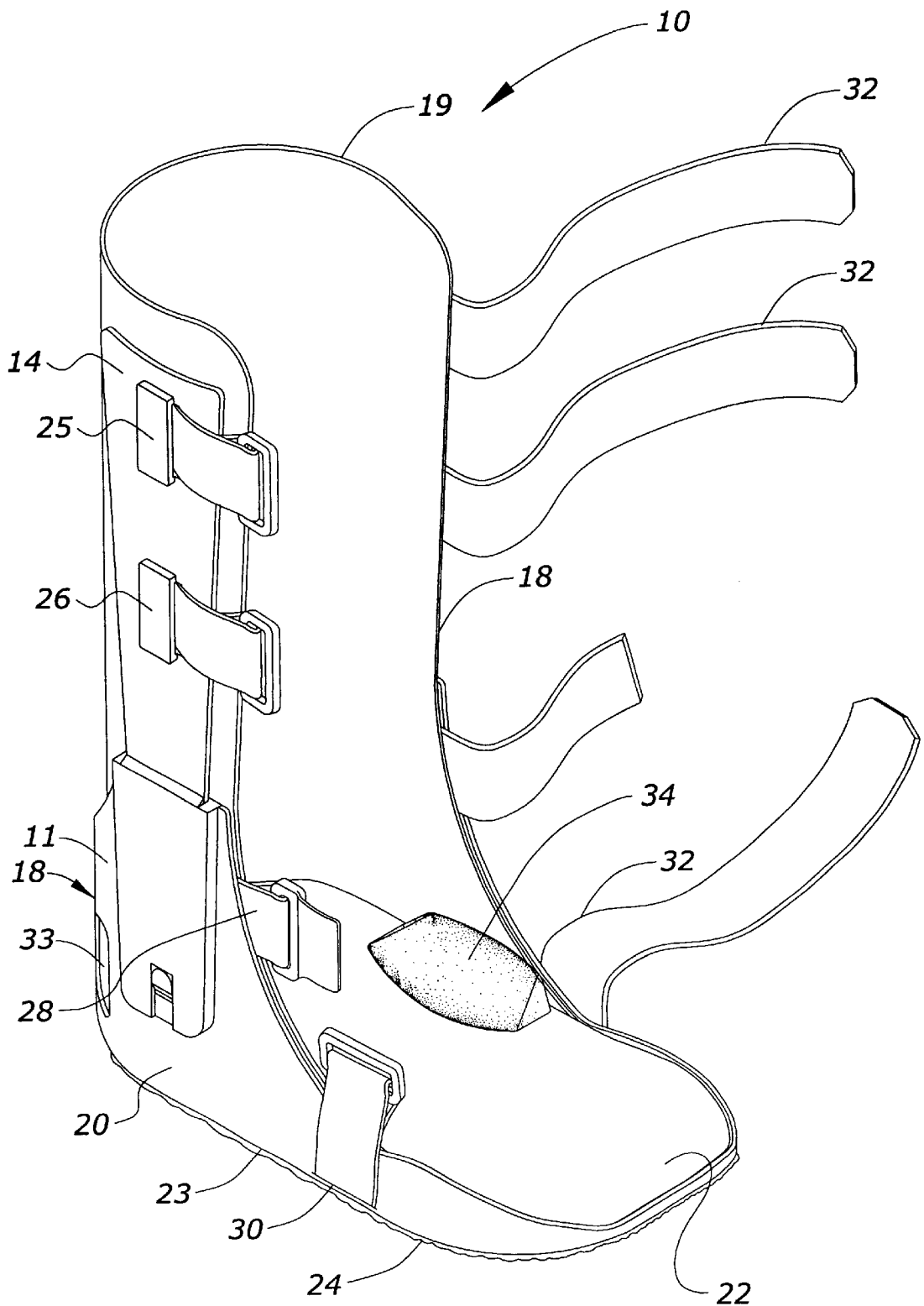
FIG. 4 shows how the arch support can be attached to turn the left splint of FIG. 1 into a properly conformed right foot splint, with arch support.

As best illustrated in FIGS. 3 and 4, an arch support 34 is composed of an inner arch conforming shaped compressible material 34 with an exterior covering 36. On the bottom side of arch support 34 is a peel-off cover 38 which can be peeled away to reveal an adhesive layer 40. Adhesive layer 40 is of known adhesive material, and such may be purchased from 3M Company. Its use allows arch support 34 to be movably and removably attached to sole insert 22.

In actual operation, the device works in the following manner. Typically the patient will put on a calf stocking to eliminate skin irritation. The foot, whether right foot or left foot, is placed on the boot of the insole, with the heel fully back. Thereafter, arch support 34 is opened, and cover layer 38 peeled off to expose the adhesive 40. Arch support 34 is then positioned under the arch of either the left foot or the right foot, depending upon which foot is being placed in ankle splint 10. The front or anterior tongue member 12 is placed in position. The ankle strap 32 passing through slot 28 is fastened first, locking down the ankle, thereafter the leg straps, and finally the foot strap. All straps 32 are then readjusted for fit and comfort.

With this new improved product, a clinic does not need to have an inventory of left and right units. Instead, a clinic needs just one unit that can be made left or right by the determination of the physician or orthopaedic technologist. The physician simply removes the adhesive backing cover 40 on the bottom of the enclosed arch support 34 and attaches it to the inner sole of pad 22 of the boot to precisely fit the required arch location of the patient. By doing this, the normal gait of the patient is preserved, thus relieving stress on the foot and leg while recovering from fracture or sprain. Among the many benefits to the patient are easy adjustment for precise fit, properly located arch support to prevent improper movement of foot and lower leg, and the unit allows a natural gait.

While a preferred embodiment of the invention is described and illustrated herein, it will be understood by those of ordinary skill in the art and others that several changes can be made to the illustrated embodiment while remaining within the spirit and scope of the present invention. For example, a wide variety of materials can be used in the manufacture of the splint as long as the rigidity of the members is maintained. Further, while hook and loop fastening straps of the Velcro type have been illustrated, other fastening straps are possible. Also, the shell here described is a preferred embodiment only and may be altered and still make use of the adjustable arch support. The dimensions given herein are exemplary only and are not intended to limit the scope of the invention. The invention, therefore, should be defined solely by reference to the appended claims, and the proper range of equivalents to which they are entitled.

What is claimed is:

1. A universal walking splint, removably attachable to the lower leg and foot to substantially immobilize the ankle joint comprising:

a posterior shell of substantially rigid material adapted to conform to the lower leg, around the heel and the bottom of the foot;

an anterior member of substantially rigid material adapted for placement on the front of said leg, said anterior member conforming generally to the front portion of the lower leg and a portion of the top of the foot;

a sole insert pad positioned in the posterior shell under the foot; and an arch support movably and removably attachable to said sole insert pad to provide selectively arch support under either a right foot or a left foot.

2. The universal walking splint of claim 1 wherein the anterior shell has a medial upright member and a lateral upright member.

3. The universal walking splint of claim 2 wherein at least two straps are vertically spaced from one another along the posterior shell and are operable to encircle the upright members to selectively apply tension to hold said members against the leg.

4. The universal walking splint of claim 3 wherein the posterior shell has a strap extending from the medial side of the sole portion to the anterior side operable to encircle the top of the foot to selectively apply tension to hold the anterior member and the posterior member against the foot.

5. The universal walking splint of claim 1 wherein the arch support is made of compressible foam, having an adhesive backing for removable and movable attachment to the sole insert pad.

* * * * *